US00PP27554P3

(12) United States Plant Patent
Wood

(10) Patent No.: US PP27,554 P3
(45) Date of Patent: Jan. 17, 2017

(54) ***ILEX* PLANT NAMED 'SMNIGAB17'**

(50) Latin Name: *Ilex glabra*
Varietal Denomination: SMNIGAB17

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 74 days.

(21) Appl. No.: 14/545,045

(22) Filed: Mar. 19, 2015

(65) Prior Publication Data

US 2016/0278265 P1 Sep. 22, 2016

(51) Int. Cl.
*A01H 5/00* (2006.01)

(52) U.S. Cl.
USPC ..... Plt./247

(58) Field of Classification Search
USPC ..... Plt./226, 247
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct *Ilex* plant named 'SMNIGAB17', characterized by its compact, uniform and low mounding plant habit; freely branching habit; dense and bushy growth habit; small dark green-colored leaves; developing leaves greyed orange in color; and good garden performance and winter hardiness.

2 Drawing Sheets

Botanical designation: *Ilex glabra*.
Cultivar denomination: 'SMNIGAB17'.

BACKGROUND OF THE INVENTION

The present Invention relates to a new and distinct *Ilex* plant, botanically known as *Ilex glabra* and hereinafter referred to by the name 'SMNIGAB17'.

The new *Ilex* plant is a product of a planned breeding program conducted by the Inventor in Grand Haven, Mich. The objective of the breeding program was to develop new dwarf and compact *Ilex* plants that are winter-hardy.

The new *Ilex* plant originated from an open-pollination in May, 2007 of *Ilex glabra* 'UMASS', not patented, as the female, or seed, parent with an unknown selection of *Ilex glabra*, as the male, or pollen, parent. The new *Ilex* plant was discovered and selected by the Inventor in June, 2010 as a single plant within the progeny of the stated open-pollination in a controlled environment in Grand Haven, Mich.

Asexual reproduction of the new *Ilex* plant by softwood cuttings in Grand Haven, Mich. since June, 2010 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'SMNIGAB17'. These characteristics in combination distinguish 'SMNIGAB17' as a new and distinct *Ilex* plant:

1. Compact, uniform and low mounding plant habit.
2. Freely branching habit; dense and bushy growth habit.
3. Small dark green-colored leaves; developing leaves greyed orange in color.
4. Good garden performance and winter hardiness.

Plants of the new *Ilex* differ from plants of the female parent, 'UMASS', in the following characteristics:

1. Plants of the new *Ilex* are more compact, low mounding and uniform than plants of 'UMASS'.
2. Plants of the new *Ilex* have better winter hardiness than plants of 'UMASS'.

Plants of the new *Ilex* can be compared to the plants of *Ilex glabra* 'Shamrock', not patented. In side-by-side comparisons conducted in Grand Haven, Mich., plants of the new *Ilex* differed from plants of 'Shamrock' in the following characteristics:

1. Plants of the new *Ilex* were more compact, low mounding and uniform than plants of 'Shamrock'.
2. Plants of the new *Ilex* had smaller leaves than plants of 'Shamrock'.
3. Plants of the new *Ilex* and 'Shamrock' differed in developing leaf color as plants of 'Shamrock' had green-colored developing leaves.

BRIEF DESCRIPTION OF THE PHOTOGRAPHS

The accompanying colored photographs illustrate the overall appearance of the new *Ilex* plant. The photographs show the colors as true as it is reasonably possible to obtain in colored reproductions of this type. Colors in the photographs may differ slightly from the color values cited in the detailed botanical description, which accurately describe the colors of the new *Ilex* plant.

The photograph on the first sheet is a side perspective view of a typical plant of 'SMNIGAB17'.

The photograph on the second sheet is a close-up view of a typical plant of 'SMNIGAB17'.

DETAILED BOTANICAL DESCRIPTION

The aforementioned photographs and following observations and measurements describe plants grown during the late spring in ground beds and one-gallon containers in a polypropylene-covered shadehouse in Grand Haven, Mich. and under cultural practices typical of commercial *Ilex* production. During the production of the plants, day temperatures ranged from 18° C. to 27° C. and night temperatures ranged from ranged from 5° C. to 10° C. Plants were two years old when the photographs and detailed description were taken. In the following description, color references are made to The Royal Horticultural Society Colour Chart, 1995 Edition, except where general terms of ordinary dictionary significance are used.

Botanical classification: *Ilex glabra* 'SMNIGAB17'.

Parentage:

*Female, or seed, parent.*—*Ilex glabra* 'UMASS', not patented.

*Male, or pollen, parent.*—Unknown selection of *Ilex glabra*, not patented.

Propagation:

*Type.*—By softwood cuttings.

*Time to initiate roots, winter.*—About one month at temperatures about 27° C.

*Time to produce a rooted young plant, summer.*—About five months at temperatures about 27° C.

*Root description.*—Fine, fibrous; creamy white to brown in color.

*Rooting habit.*—Freely branching; medium density to dense.

Plant description:

*Plant and growth habit.*—Perennial evergreen shrub; compact, uniform and low mounding plant habit; vigorous growth habit.

*Branching habit.*—Freely branching habit; dense and bushy growh habit with about 19 lateral branches developing per plant.

*Plant height.*—About 27 cm.

*Plant diameter, area of spread.*—About 56 cm.

*Lateral branch description.*—Length: About 13 cm to 20 cm. Diameter: About 2 mm. Internode length: About 1 cm. Strength: Moderately strong. Texture: Smooth, glabrous. Color: Close to 145A.

*Leaf description.*—Arrangement: Alternate, simple. Length: About 3.5 cm to 4 cm. Width: About 9 mm to 13 mm. Shape: Oblanceolate to lanceolate. Apex: Acute. Base: Attenuate. Margin: Entire to serrulate. Venation pattern: Pinnate. Texture, upper surface: Smooth, glabrous; leathery; slightly waxy. Texture, lower surface: Smooth, glabrous; leathery. Color: Developing leaves, upper surface: Close to 175A. Developing leaves, lower surface: Close to 147C. Fully expanded leaves, upper surface: Close to 139A; venation, close to 145B. Fully expanded leaves, lower surface: Close to 137C; venation, close to 137C. Petioles: Length: About 5 mm. Diameter: About 1 mm. Texture, upper and lower surfaces: Smooth, glabrous. Color, upper and lower surfaces: Close to 145B.

Flower description:

*Flower appearance and arrangement.*—Single axillary rotate flowers; flowers face upright to outwardly; flowers inconspicuous; about eleven flowers develop per lateral branch.

*Natural flowering season.*—Plants flower in mid-spring in Michigan; flowers not persistent.

*Fragrance.*—None detected.

*Flower diameter.*—About 7 mm.

*Flower length (height).*—About 2 mm.

*Flower buds.*—Length: About 2 mm. Diameter: About 1.5 mm. Shape: Globular. Color: Close to 155A.

*Petals.*—Quantity and arrangement: About eight in a single whorl; fused at the base. Length: About 3 mm. Width: About 2 mm. Shape: Oblong to obovate. Apex: Obtuse. Base: Obtuse, fused. Margin: Entire. Texture, upper and lower surfaces: Smooth, glabrous. Color: When opening, upper and lower surfaces: Close to 155A. Fully opened, upper and lower surfaces: Close to 155A; color does not change with development.

*Sepals.*—Quantity and arrangement: About eight in a single whorl; fused at the base. Length: About 1 mm. Diameter: About 1 mm. Shape: Ovate. Apex: Acute. Base: Truncate, fused. Margin: Entire. Texture, upper and lower surfaces: Smooth, glabrous. Color, upper and lower surfaces: Close to 144C.

*Peduncles.*—Length: About 6 mm. Diameter: About 0.5 mm. Aspect: Upright to outwardly. Strength: Moderately strong. Texture: Smooth, glabrous. Color: Close to 144A.

*Reproductive organs.*—Androecium: Quantity per flower: About eight. Filament length: About 1 mm. Filament color: Close to 155D. Anther length: About 0.5 mm. Anther shape: Round. Anther color: Close to 155D. Pollen amount: Scarce. Pollen color: Close to 155D. Gynoecium: Quantity per flower: One. Pistil length: About 1 mm. Style length: About 0.5 mm. Style color: Close to 144A. Stigma shape: Globular with three lobes. Stigma color: Close to 144B. Ovary color: Close to 144A.

*Seeds and fruits.*—Seed and fruit development have not been observed on plants of the new *Ilex*.

Garden performance: Plants of the new *Ilex* have been observed to have good garden performance and to be tolerant to rain, wind and temperatures ranging from about −25° C. to about 35° C.

Pathogen & pest resistance: Plants have not been observed to be resistant to pathogens and pests common to *Ilex* plants.

It is claimed:

1. A new and distinct *Ilex* plant named 'SMNIGAB17' as illustrated and described.

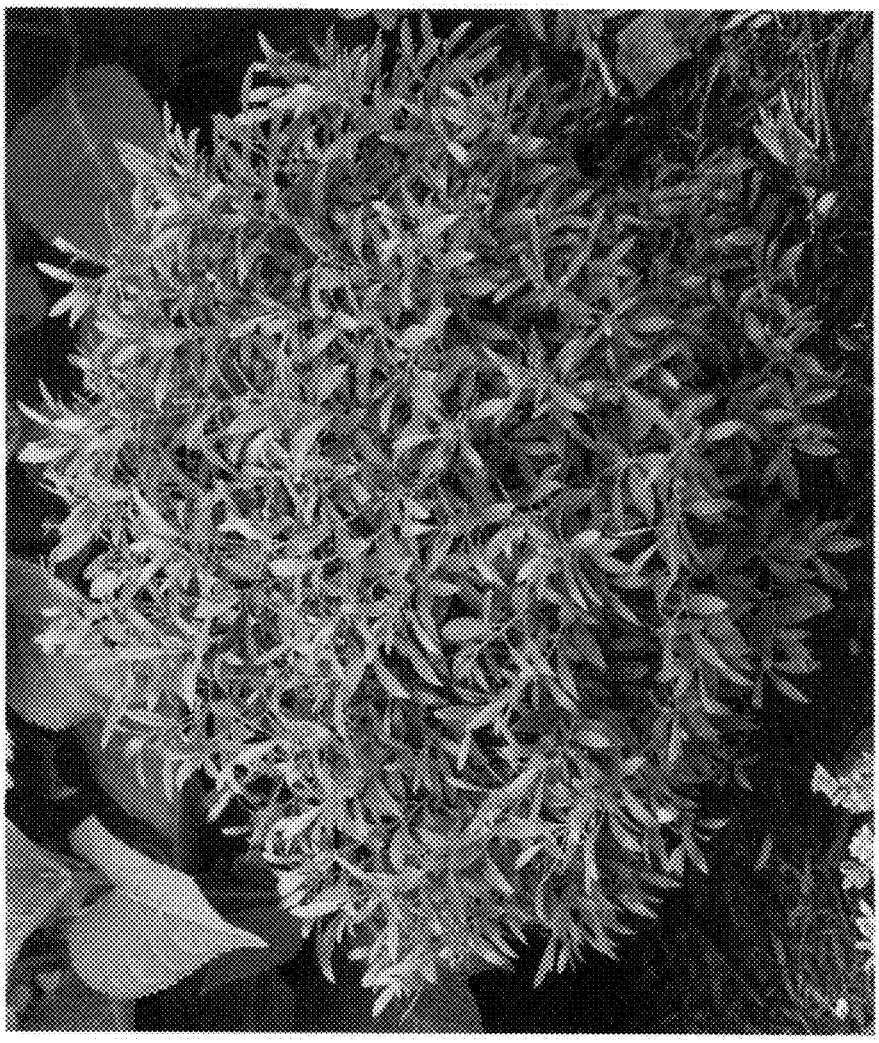

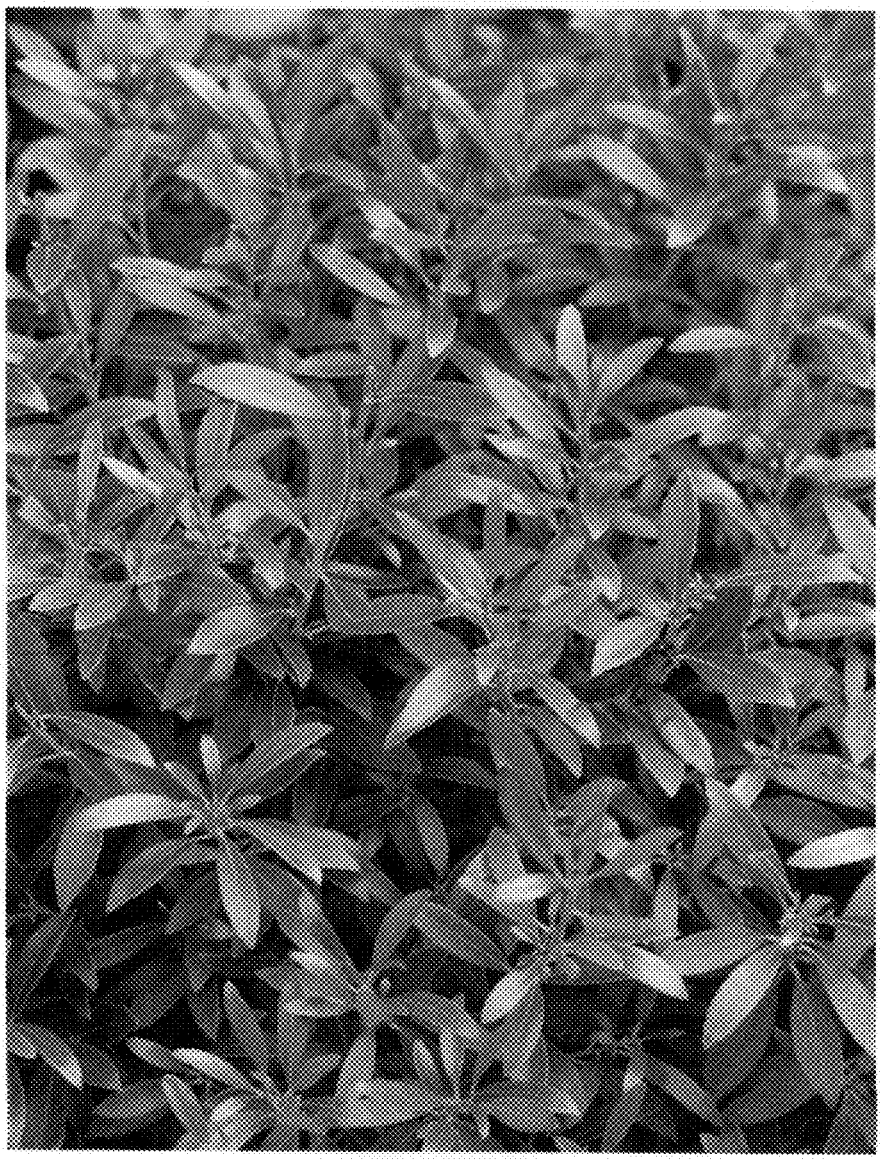

* * * * *